United States Patent
Cao et al.

(10) Patent No.: US 7,530,808 B2
(45) Date of Patent: May 12, 2009

(54) BINARY DENTAL BLEACHING USING SWITCH-CLOSABLE DOUBLE BARREL SYRINGE

(75) Inventors: Densen Cao, Sandy, UT (US); Calvin D. Ostler, Riverton, UT (US); Robert K. Larsen, Sandy, UT (US)

(73) Assignee: CAO Group, Inc, West Jordan, UT (US)

( * ) Notice: Subject to any disclaimer, the term of this patent is extended or adjusted under 35 U.S.C. 154(b) by 234 days.

(21) Appl. No.: 10/945,550

(22) Filed: Sep. 20, 2004

(65) Prior Publication Data

US 2005/0202365 A1 Sep. 15, 2005

Related U.S. Application Data

(63) Continuation-in-part of application No. 10/797,628, filed on Mar. 10, 2004, now abandoned.

(51) Int. Cl.
*A61C 5/04* (2006.01)
*B67D 5/60* (2006.01)

(52) U.S. Cl. ...................... 433/89; 222/145.5

(58) Field of Classification Search ................... 433/89, 433/215; 222/145.5, 145.6; 366/181.5
See application file for complete search history.

(56) References Cited

U.S. PATENT DOCUMENTS

| | | | | |
|---|---|---|---|---|
| 3,369,934 | A | * | 2/1968 | Pollard ........................ 134/3 |
| 3,966,090 | A | * | 6/1976 | Prussin et al. ................ 222/94 |
| 4,432,469 | A | * | 2/1984 | Eble et al. .................... 222/134 |
| 4,846,373 | A | * | 7/1989 | Penn et al. ................... 222/137 |
| 4,969,747 | A | * | 11/1990 | Colin et al. ................. 366/339 |
| 5,301,842 | A | * | 4/1994 | Ritter ......................... 222/137 |
| 5,928,628 | A | * | 7/1999 | Pellico ........................ 424/49 |
| 5,944,226 | A | * | 8/1999 | Schiltz et al. ............... 222/137 |
| 6,116,900 | A | | 9/2000 | Ostler |
| 6,500,408 | B2 | * | 12/2002 | Chen ........................... 424/53 |
| 6,732,887 | B2 | | 5/2004 | Bills |

\* cited by examiner

*Primary Examiner*—John J Wilson
(74) *Attorney, Agent, or Firm*—Geoffrey E. Dobbin

(57) ABSTRACT

The present invention is a switch-closeable double barrel syringe and methods for bleaching teeth using it. The syringe comprises two separately contained barrels, each containing one component of a dental bleach, and a rotatable tip with orifices to match, when open, orifices in the barrels, and a mixing chamber. The tip rotates between open and closed positions in order to dispense bleaching compositions for use in dental hygiene. Various formulations of bleaching compositions may be contained within the barrels, however the invention is ideally suited for those which require separate storage of active ingredients before use.

22 Claims, 4 Drawing Sheets

BINARY DENTAL BLEACHING USING SWITCH-CLOSABLE DOUBLE BARREL SYRINGE

PRIORITY

This patent application is a continuation-in-part of U.S. patent application Ser. No. 10/797,628 filed on Mar. 10, 2004 now abandoned, which is hereby incorporated by reference.

BACKGROUND

In the field of dental whitening, two part dental bleaches which are mixed just prior to application to teeth are often more effective and pre-mixed one part dental bleaches. Consequently, it is desirable to have a simple method for mixing and dispensing the two parts of the dental bleach without mess or hassle.

SUMMARY

A switch-closable double barrel syringe and methods for bleaching teeth using it are disclosed.

DETAILED DESCRIPTION

Figure 1:
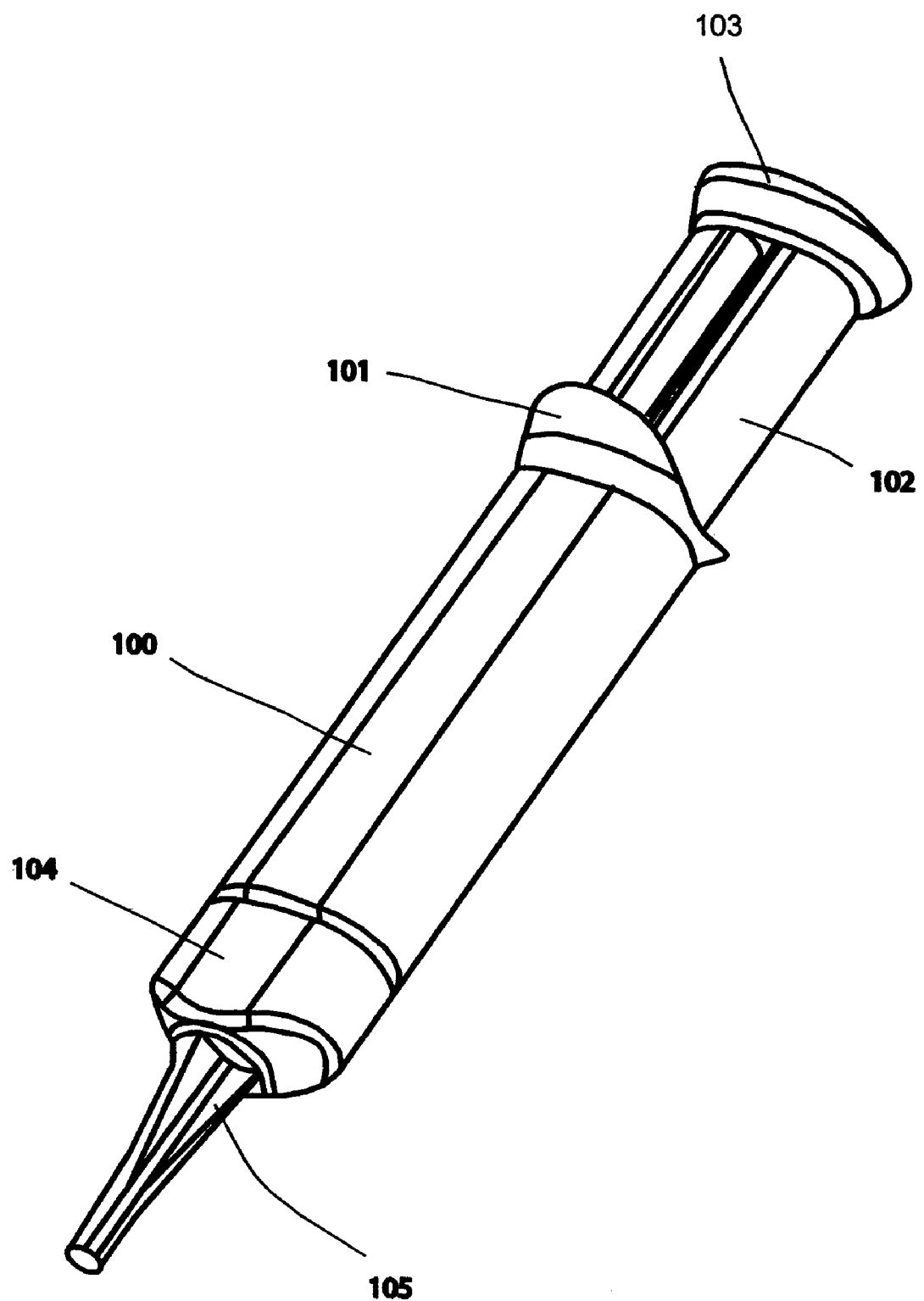
FIG. 1 depicts a switch-closable double barrel syringe for use in dental whitening with the switch in its open position.

In the field of dental bleaching, it is desirable to provide a dental bleach which is fast acting and powerful in order to bleach teeth very quickly. One-part dental bleaches in the past were dispensed from single barrel syringes, but were slow-acting and often had to be worn in a dental tray overnight for a month or two at a time, and still did not achieve a satisfactory whitening effect. Such a system is illustrated in the Opalescence Tooth Whitening System available from Ultradent Products, Inc. of South Jordan, Utah.

Some effort has been made to accelerate the speed of dental bleaching.

One such effort utilized a binary dental bleach in which one bleach component included a whitening agent, and the other included a basic substance to accelerate dental whitening. Such a system is found in U.S. Pat. No. 6,116,900 which is hereby incorporated by reference. However, that system, once opened, is subject to leaks and mess. Also, it does not provide the very rapid dental bleaching that dental patients desire.

A more advanced dental whitening system uses a two part (or multi-part) dental bleach which includes a whitening agent and an accelerator. The whitening agent includes oxygen which can be released as oxygen radicals that bond to organic stain molecules on teeth in order to whiten the teeth. Examples of oxygen-containing medium which may be present in a whitening agent include hydrogen peroxide and carbamide peroxide. The accelerator includes a substance which chemically reacts with the whitening agent in order to accelerate release of oxygen ions, or to cause release of more oxygen ions than would be released without use of the accelerator. Example accelerators include KI, KBr and KOH iodide ions. The addition of the iodide ion by way of potassium iodide to a peroxide such as hydrogen peroxide in a basic medium yields free radical oxygen and water, generating large amounts of heat and depleting the oxygen containing medium such as hydrogen peroxide in a matter of minutes and providing a rapid dental bleaching effect.

Some example two part dental bleaches which could be used with the switch-closeable double barrel syringe are below.

EXAMPLE 1

Hypromellose 2208 Containing Tooth Whitening Gel

| Ingredient | Energizer Phase % by weight | Peroxide Phase % by weight |
| --- | --- | --- |
| Hypromellose 2208 | 2.0 | 2.0 |
| Glycerin | 30.0 | 34.0 |
| Potassium Hydroxide | 0.066 | 0.0 |
| Potassium Iodide | 0.90 | 0.0 |
| Hydrogen Peroxide, 50% aqueous | 0.0 | 32.0 |
| Ion Scavenger (Di-sodium EDTA) | 0.0 | 0.1-5 |
| Sweetener (saccharin) | 1.0 | 0.0 |
| Flavoring (Oil of Peppermint) | 1.0 | 0.0 |
| Additional Ingredients (Dyes, Indicators, etc) | 0.0-10.0 | 0.0 |
| Deionized or Distilled Water | (QS) | (QS) |

EXAMPLE 2

Polyvinyl Alcohol Containing Tooth Whitening Gel

| Ingredient | Energizer Phase % by weight | Peroxide Phase % by weight |
| --- | --- | --- |
| Polyvinyl Alcohol | 10.0 | 10.0 |
| Glycerin | 32.0 | 34.0 |
| Potassium Hydroxide | 0.066 | 0.0 |
| Potassium Iodide | 0.90 | 0.0 |
| Hydrogen Peroxide, 50% aqueous | 0.0 | 32.0 |
| Ion Scavenger (Di-sodium EDTA) | 0.0 | 0.1-5 |
| Sweetener (saccharin) | 1.0 | 0.0 |
| Flavoring (Oil of Peppermint) | 1.0 | 0.0 |
| Additional Ingredients (Dyes, Indicators, etc) | 0.0-10.0 | 0.0 |
| Deionized or Distilled Water | (QS) | (QS) |

EXAMPLE 3

Polyvinylpyrrolidone Containing Tooth Whitening Gel

| Ingredient | Energizer Phase % by weight | Peroxide Phase % by weight |
| --- | --- | --- |
| Polyvinylpyrrolidone | 32.0 | 33.0 |
| Glycerin | 32.0 | 34.0 |
| Potassium Hydroxide | 0.066 | 0.0 |
| Potassium Iodide | 0.90 | 0.0 |

-continued

| Ingredient | Energizer Phase % by weight | Peroxide Phase % by weight |
|---|---|---|
| Hydrogen Peroxide, 50% aqueous | 0.0 | 32.0 |
| Ion Scavenger (Di-sodium EDTA) | 0.0 | 0.1-5 |
| Sweetener (saccharin) | 1.0 | 0.0 |
| Flavoring (Oil of Peppermint) | 1.0 | 0.0 |
| Additional Ingredients (Dyes, Indicators, etc) | 0.0-10.0 | 0.0 |
| Deionized or Distilled Water | (QS) | (QS) |

EXAMPLE 4

Generic Tooth Whitening Gel

| Ingredient | Energizer Phase % by weight | Peroxide Phase % by weight |
|---|---|---|
| Thickener | 0-90% | 0-90% |
| Additional thickener(s) | 0-90% | 0-90% |
| Basic substance | 0-10% | 0-10% |
| Additional basic substance(s) | 0-10% | 0-10% |
| Oxygen-containing substance (such as peroxide) | 0% | 0-80% |
| Ion Scavenger | 0-10% | 0-10% |
| Sweetener and Flavoring | 0-10% | 0-10% |
| Additional Ingredients (Dyes, Indicators, etc) | 0.0-10.0% | 0.0-10% |
| Other (water, etc.) | 0-50% | 0-50% |

Referring to Figure a switch-closable double barrel syringe for use in dental whitening with the switch in its closed position is depicted. It includes an elongate reservoir section 100 that has two separate chambers for two parts of a binary dental bleach. A handle 101 is provided to hold while depressing a plunger 102 via plunger butt 103 to dispense whitener from the syringe. When the plunger is depressed, whitener components are forced through the closeable switch 104 on which is attached a mixing tip 105 which mixes the components of the bleach for application to teeth.

Figure 2:
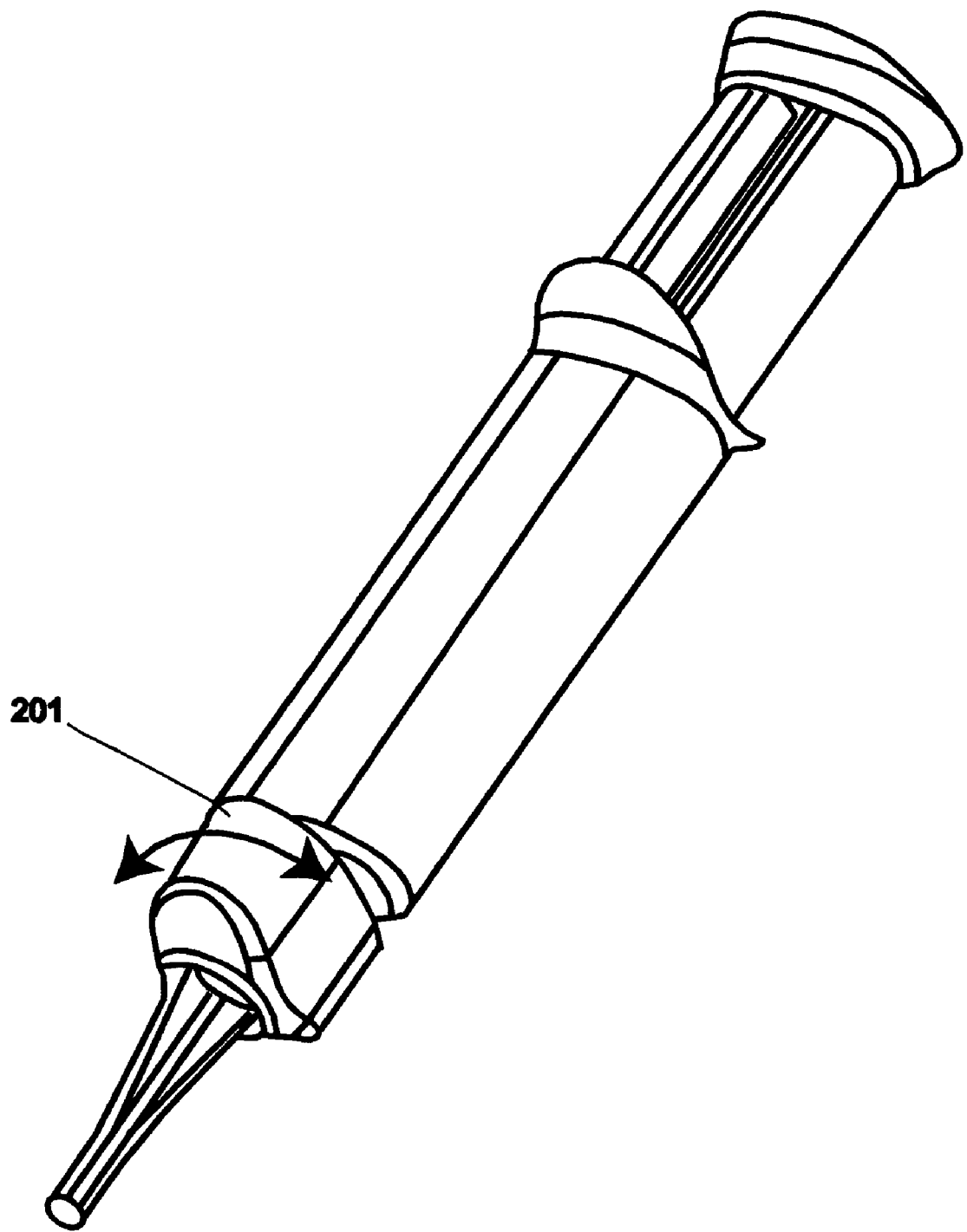
FIG. 2 depicts a switch-closable double barrel syringe for use in dental whitening with the switch in its closed position.

FIG. 2 depicts a switch-closable double barrel syringe for use in dental whitening with the switch in its open position. The closeable switch 201 is shown being capable of rotating in two directions with respect to the longitudinal axis of the syringe in order to open and close the syringe chambers for dispensing whitener or terminating the dispensing thereof.

Figure 3:
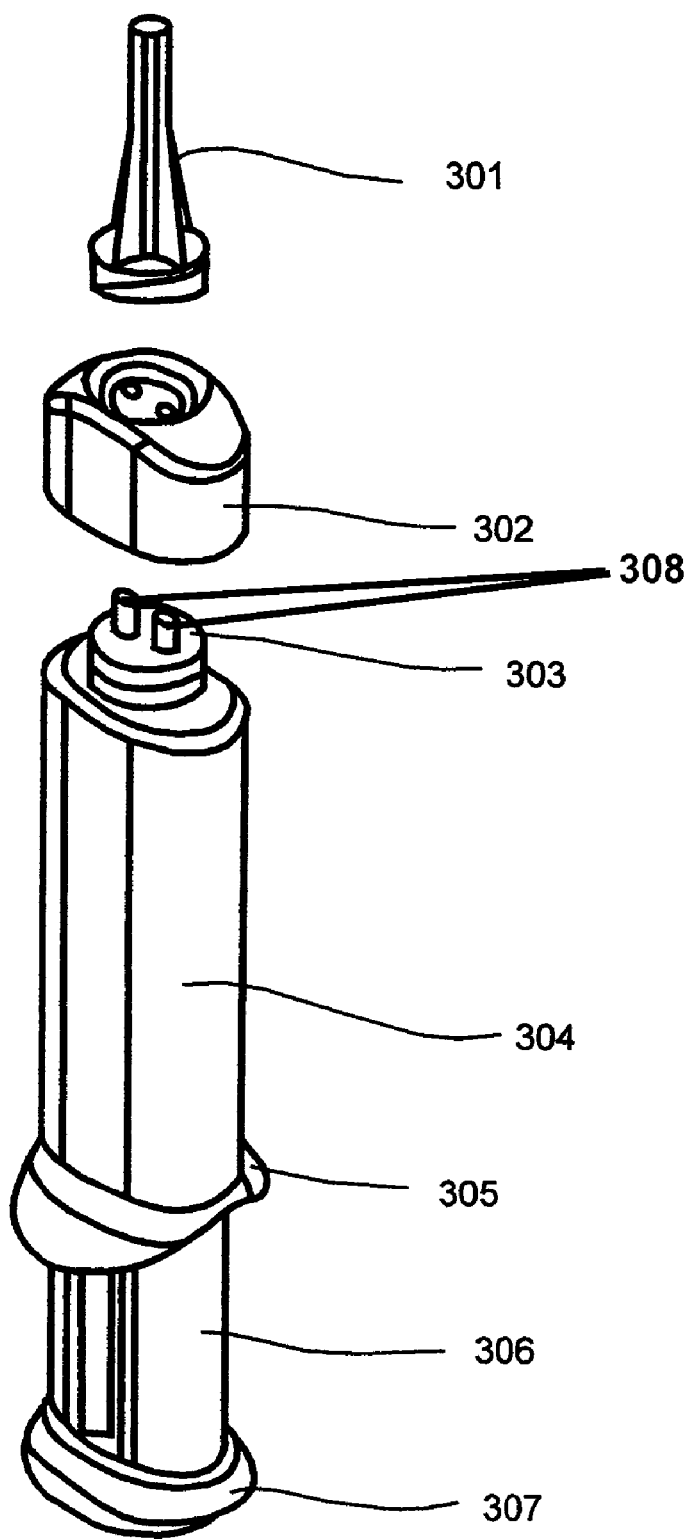
FIG. 3 depicts assembly of a switch-closeable double barrel syringe for use in dental bleaching.

FIG. 3 depicts assembly of a switch-closeable double barrel syringe for use in dental bleaching. It includes a mixing tip 301 and a rotatably closeable switch 302. Exit orifices 308 are located upon switch pedestal 303. Whitener components exit the reservoirs, or barrels, 304, through exit orifices 308 and enter the mixing tip 301. A handle 305, a dual plunger arrangement 306 and a plunger butt 307 are provided for exerting force thereagainst and for dispensing whitener.

Figure 4:
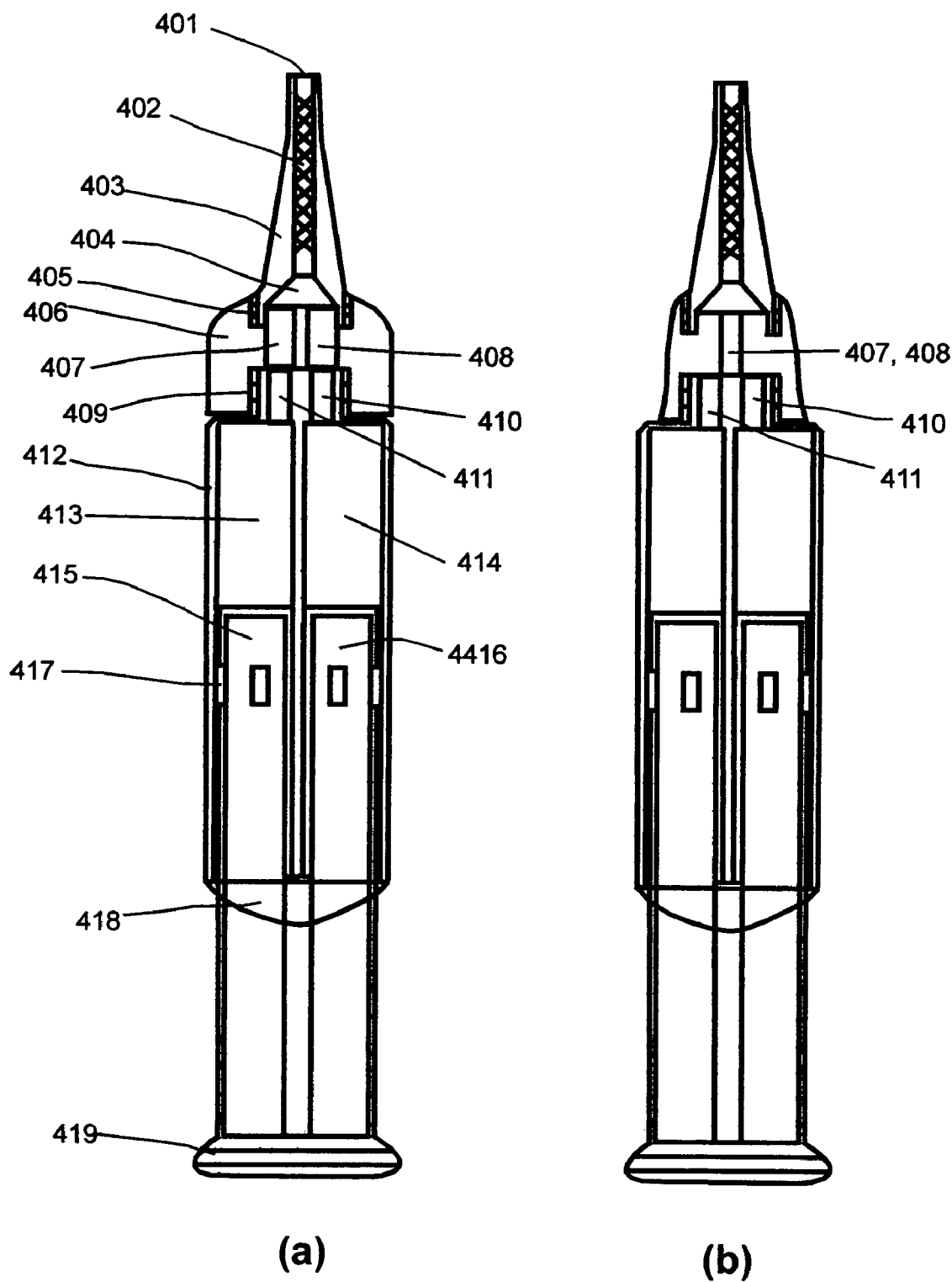
FIGS. 4a and 4b depict cross sectional side views of a switch-closeable double barrel syringe with the switch in its open (FIG. 4a) and closed (FIG. 4b) positions.

FIGS. 4a and 4b depict cross sectional side views of a switch-closeable double barrel syringe with the switch in its open (FIG. 4a) and closed (FIG. 4b) positions. A plunger butt 419 and handle 418 are provided to permit force to be applied to the plungers to dispense whitener. The plungers 415 and 416 are located within barrels, chambers or reservoirs 413 and 414. There is an air release gap 417 between the plungers and the barrel wall 412. Each barrel has an outlet or exit orifice 410 and 411 through which bleach components may be dispensed. When the switch is in its open position, the exit orifices 410 and 411 line up with conduction paths 407 and 408 and permit bleach components to travel through the closeable switch to the mixing tip 402. When the closeable switch is in the closed position, the exit orifices of the barrels do not line up with the conduction paths, and the syringe assembly is sealed. The closeable switch 406 is affixed to the barrel assembly via a push lock located on switch pedestal 409. The rotatably closeable switch has a luer lock fitting 405 to permit the mixing tip to be installed thereon. The mixing tip 402 mixes bleach components so that from its output hole 401, there emits a mixed and ready to use dental bleach.

The bleach may be applied to teeth via various means, including by use of a dental tray.

While apparatuses, compositions and methods have been described and illustrated in conjunction with a number of specific ingredients, materials and configurations herein, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of snacks described herein are to be considered in all respects as only illustrative, and not restrictive. All changes which come within the meaning and range of equivalency of the claims are to be embraced within their scope.

We claim:

1. A two part dental bleaching system comprising:
 a switch-closeable double barrel syringe having two barrels for containing bleaching components,
 a whitening agent in one of said barrels, said whitening agent containing a peroxide,
 an energizer in another of said barrels, said energizer containing a compound of iodine,
 plungers in each of said barrels,
 exit orifices for each of said barrels that pass through a switch pedestal and through which bleaching components may exit,
 a rotabably openable and closeable switch located adjacent said barrels on the switch pedestal, said switch having one half of a luer-type connector and two conduits that selectively will allow the whitening agent and the energizer to pass through the switch;
 a mixing tip, having an exit orifice on one end and a mating half of a luer-type connector on another end, said tip and said switch capable of joining with the luer-type connector halves;
 said tip having a conduit in it through which bleaching components may travel and a mixing chamber located within said tip for mixing said whitening agent and said energizer as they pass through the switch conduits in order to form a mixed dental bleach leaving said switch-closeable double barrel syringe,
 said barrel exit orifices lining up with said tip conduits when said tip is in an open position, and
 said barrel exit orifices not lining up with said tip conduits when said tip is in a closed position.

2. A system as recited in claim 1 wherein said energizer contains an energizer substance that will chemically react with an oxygen-containing medium in said whitening agent to cause release of oxygen ions therefrom at a rate that is greater than a rate of release of oxygen ions from said whitening agent absent said energizer.

3. A system as recited in claim 1 wherein said whitening agent is selected from the group consisting of hydrogen peroxide and carbamide peroxide.

4. A system as recited in claim 1 wherein said energizer includes a basic substance.

5. A system as recited in claim 1 wherein said energizer includes potassium hydroxide.

6. A system as recited in claim 1 wherein said energizer includes potassium iodide.

7. A system as recited in claim 1 wherein said energizer includes both potassium hydroxide and potassium iodide.

8. A system as recited in claim 1 wherein said energizer includes a compound of potassium.

9. A system as recited in claim 1 wherein said energizer includes a hydroxide and an iodide.

10. A system as recited in claim 1 wherein said energizer includes a thickener.

11. A system as recited in claim 1 wherein said thickener is selected from the group consisting of polyvinylpyrrolidone, polyvinyl alcohol and glycerin.

12. A method for bleaching teeth using a switch-closeable double barrel syringe comprising the steps of:

obtaining a switch-closeable double barrel syringe having
a switch-closeable double barrel syringe having two barrels for containing bleaching components,
a whitening agent in one of said barrels, said whitening agent containing a peroxide,
an energizer in another of said barrels, said energizer containing a compound of iodine,
plungers in each of said barrels,
exit orifices for each of said barrels that pass through a switch pedestal and through which bleaching components may exit,
a rotabably openable and closeable switch located adjacent said barrels on the switch pedestal, said switch having one half of a luer-type connector and two conduits that selectively will allow the whitening agent and the energizer to pass through the switch;
a mixing tip, having an exit orifice on one end and a mating half of a luer-type connector on another end, said tip and said switch capable of joining with the luer-type connector halves;
said tip having a conduit in it through which bleaching components may travel and a mixing chamber located within said tip for mixing said whitening agent and said energizer as they pass through the switch conduits in order to form a mixed dental bleach leaving said switch-closeable double barrel syringe,
said barrel exit orifices lining up with said tip conduits when said tip is in an open position, and
said barrel exit orifices not lining up with said tip conduits when said tip is in a closed position,
rotating said switch to its open position,
simultaneously mixing said whitening agent and said energizer as a mixed dental bleach,
dispensing said mixed dental bleach so that it comes into contact with teeth,
permitting said energizer to chemically react with said whitening agent to rapidly release oxygen ions therefrom, and
permitting said oxygen ions to react with organic stain molecules on teeth and remove those molecules from teeth to achieve a whitening effect.

13. A method as recited in claim 12 wherein said energizer contains an energizer substance that will chemically react with an oxygen-containing medium in said whitening agent to cause release of oxygen ions therefrom at a rate that is greater than a rate of release of oxygen ions from said whitening agent absent said energizer.

14. A method as recited in claim 12 wherein said whitening agent is selected from the group consisting of hydrogen peroxide and carbamide peroxide.

15. A method as recited in claim 12 wherein said energizer includes a basic substance.

16. A method as recited in claim 12 wherein said energizer includes potassium hydroxide.

17. A method as recited in claim 12 wherein said energizer includes potassium iodide.

18. A method as recited in claim 12 wherein said energizer includes both potassium hydroxide and potassium iodide.

19. A method as recited in claim 12 wherein said energizer includes a compound of potassium.

20. A method as recited in claim 12 wherein said energizer includes a hydroxide and an iodide.

21. A method as recited in claim 12 wherein said energizer includes a thickener.

22. A method as recited in claim 12 wherein said thickener is selected from the group consisting of polyvinylpyrrolidone, polyvinyl alcohol and glycerin.

* * * * *